United States Patent
Bajwa et al.

(10) Patent No.: US 8,063,043 B2
(45) Date of Patent: Nov. 22, 2011

(54) SALTS OF N-[6-CIS-2,6-DIMETHYLMORPHOLIN-4-YL)PYRIDINE-3-YL]-2-METHYL-4'-(TRIFLUOROMETHOXY)[1,1'-BIPHENYL]-3-CARBOXAMIDE

(75) Inventors: Joginder Bajwa, Elmwood Park, NJ (US); Marilyn de la Cruz, Matawan, NJ (US); Stephanie Kay Dodd, Ayer, MA (US); Liladhar Murlidhar Waykole, Succasunna, NJ (US); Raeann Wu, Pine Brook, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 13/061,572

(22) PCT Filed: Sep. 15, 2009

(86) PCT No.: PCT/US2009/056918
§ 371 (c)(1),
(2), (4) Date: Mar. 1, 2011

(87) PCT Pub. No.: WO2010/033481
PCT Pub. Date: Mar. 25, 2010

(65) Prior Publication Data
US 2011/0178085 A1  Jul. 21, 2011

Related U.S. Application Data

(60) Provisional application No. 61/097,580, filed on Sep. 17, 2008.

(51) Int. Cl.
*A61K 31/535* (2006.01)
*C07D 413/04* (2006.01)
(52) U.S. Cl. .................... 514/235.5; 544/131
(58) Field of Classification Search ............... 514/235.5; 544/131
See application file for complete search history.

(56) References Cited

FOREIGN PATENT DOCUMENTS
WO  2007/131201  11/2007

OTHER PUBLICATIONS

Berge Stephen M et al: "Pharmaceutical Salts", Journal of Pharmaceutical Sciences, vol. 66, No. 1, pp. 1-19, Jan. 1977.

*Primary Examiner* — Rebecca Anderson
(74) *Attorney, Agent, or Firm* — Matthew Mulkeen

(57) ABSTRACT

Salts of N-[6-(cis-2,6-dimethylmorpholin-4-yl)pyridine-3-yl]-2-methyl-4'-(trifluoromethoxy)[1,1'-biphenyl]-3-carboxamide are prepared and characterized.

2 Claims, 3 Drawing Sheets

SALTS OF N-[6-CIS-2,6-DIMETHYLMORPHOLIN-4-YL) PYRIDINE-3-YL]-2-METHYL-4'-(TRIFLUOROMETHOXY)[1,1'-BIPHENYL]-3-CARBOXAMIDE

This is a National Stage of International Application No. PCT/US2009/056918 filed on Sep. 15, 2009, which claims benefit of U.S. Provisional Application No. 61/097,580 filed Sep. 17, 2008, which in its entirety are herein incorporated by reference.

BACKGROUND OF THE INVENTION

1. Field of the Invention

This invention relates to salts of N-[6-(cis-2,6-dimethylmorpholin-4-yl)pyridine-3-yl]-2-methyl-4'-(trifluoromethoxy)[1,1'-biphenyl]-3-carboxamide, as well as to pharmaceutical compositions comprising the same and methods of treatment using the same.

2. Related Background Art

The compound N-[6-(cis-2,6-dimethylmorpholin-4-yl)pyridine-3-yl]-2-methyl-4'-(trifluoromethoxy)[1,1'-biphenyl]-3-carboxamide has the formula (I):

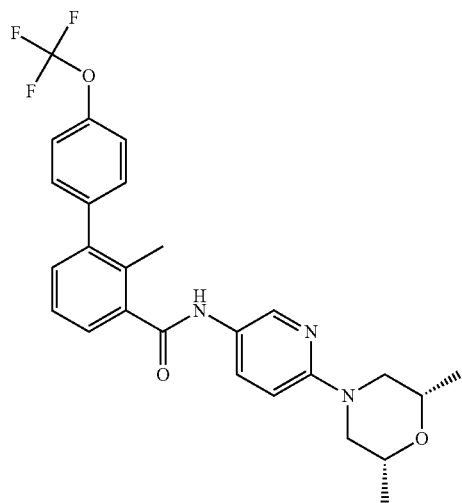

(I)

as described in WO 2007/131201. Valuable pharmacological properties are attributed to this compound; thus, it can be used, for example, as modulating the activity of the hedgehog signaling pathway useful in therapy for diseases which respond to modulating the activity of the hedgehog signaling pathway. WO 2007/131201 does not disclose any specific salts or salt hydrates or solvates of N-[6-(cis-2,6-dimethyl-morpholin-4-yl)pyridine-3-yl]-2-methyl-4'-(trifluoromethoxy)[1,1'-biphenyl]-3-carboxamide.

It has been found that the salt forms of the present invention shows that in addition to good physico-chemical properties that salts may have high permeability and high bioavailability.

SUMMARY OF THE INVENTION

The present invention is directed to salts of N-[6-(cis-2,6-dimethylmorpholin-4-yl)pyridine-3-yl]-2-methyl-4'-(trifluoromethoxy)[1,1'-biphenyl]-3-carboxamide. Preferred embodiments of the present invention are directed to the hydrochloride, diphosphate and sulfate salts of N-[6-(cis-2,6-dimethylmorpholin-4-yl)pyridine-3-yl]-2-methyl-4'-(trifluoromethoxy)[1,1'-biphenyl]-3-carboxamide.

The invention is further directed to pharmaceutical compositions comprising:

(a) a therapeutically effective amount of an inventive salt of N-[6-(cis-2,6-dimethylmorpholin-4-yl)pyridine-3-yl]-2-methyl-4'-(trifluoromethoxy)[1,1'-biphenyl]-3-carboxamide; and (b) at least one pharmaceutically acceptable carrier, diluent, vehicle or excipient.

The present invention is also directed to a method of treating a disease which responds to modulating the activity of the hedgehog signaling pathway comprising the step of administering to a subject in need of such treatment a therapeutically effective amount of an inventive salt of N-[6-(cis-2,6-dimethylmorpholin-4-yl)pyridine-3-yl]-2-methyl-4'-(trifluoromethoxy)[1,1'-biphenyl]-3-carboxamide.

DETAILED DESCRIPTION OF THE INVENTION

Figure 1:
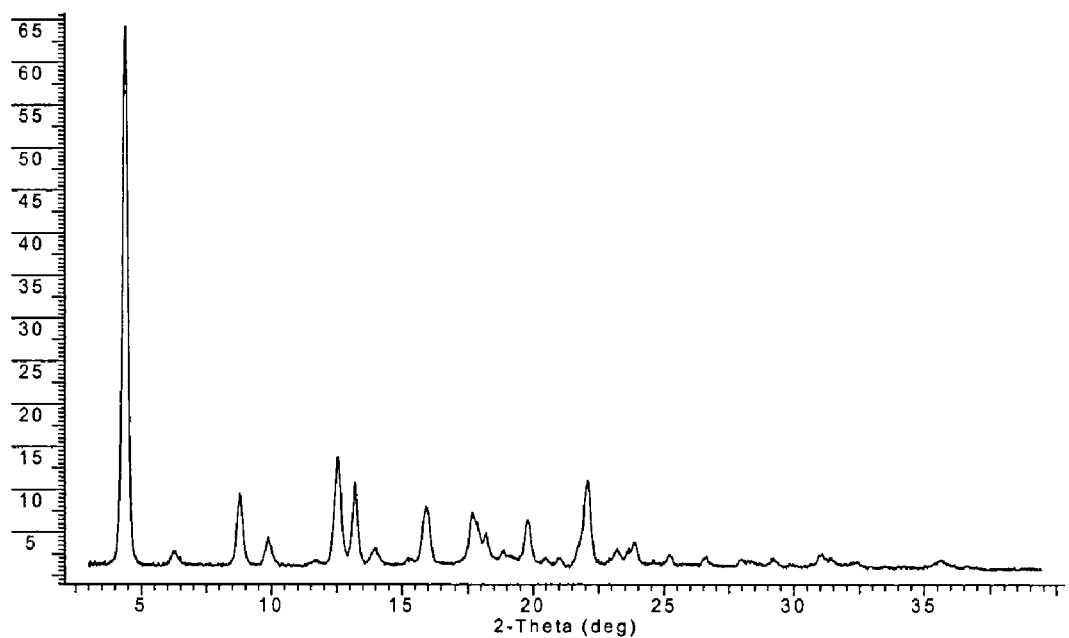
FIG. 1 shows the x-ray powder diffraction pattern for N-[6-(cis-2,6-dimethylmorpholin-4-yl)pyridine-3-yl]-2-methyl-4'-(trifluoromethoxy)[1,1'-biphenyl]-3-carboxamide diphosphate salt.
Figure 2:
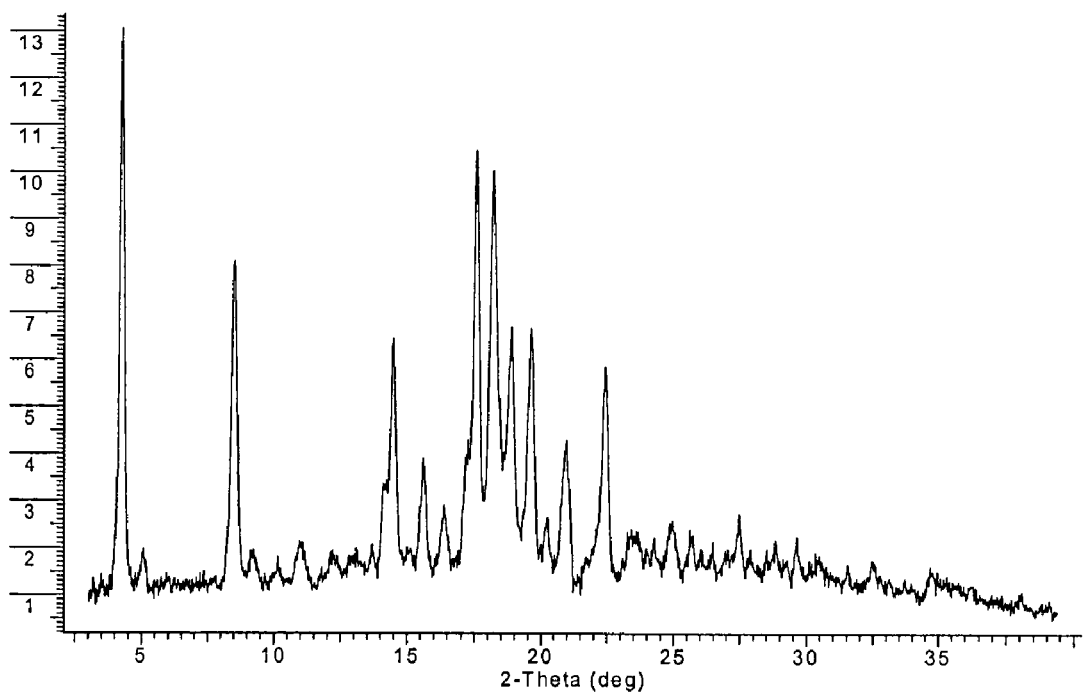
FIG. 2 shows the x-ray powder diffraction pattern for N-[6-(cis-2,6-dimethylmorpholin-4-yl)pyridine-3-yl]-2-methyl-4'-(trifluoromethoxy)[1,1'-biphenyl]-3-carboxamide monosulfate salt.
Figure 3:
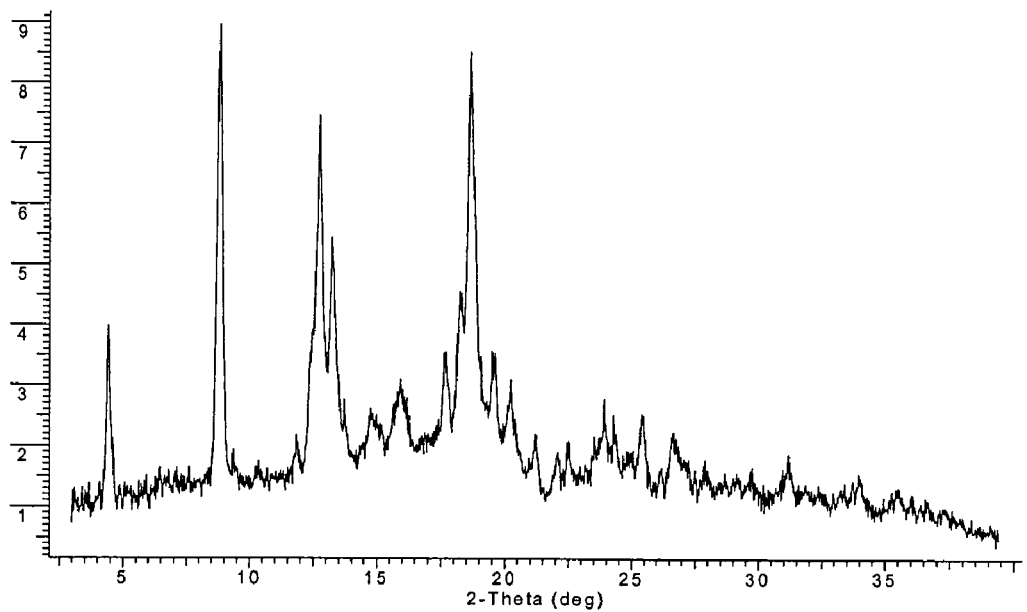
FIG. 3 shows the x-ray powder diffraction pattern for N-[6-(cis-2,6-dimethylmorpholin-4-yl)pyridine-3-yl]-2-methyl-4'-(trifluoromethoxy)[1,1'-biphenyl]-3-carboxamide monohydrochloride salt.

As used herein, "salt" refers to a compound prepared by the reaction of an organic acid or base drug with a pharmaceutically acceptable mineral or organic acid or base; as used herein, "salt" includes hydrates and solvates of salts made in accordance with this invention. Exemplary pharmaceutically acceptable mineral or organic acids or bases are as listed in Tables 1-8 in *Handbook of Pharmaceutical Salts*, P. H. Stahl and C. G. Wermuth (eds.), VHCA, Zurich 2002, pp. 334-345. In particular, salts include, but are not limited to, hydrochloride, phosphate, sulfate, mesylate, esylate and besylate salt forms. As used herein, "polymorph" refers to a distinct "crystal modification" or "polymorphic form" or "crystalline form", which differs from another with respect to x-ray powder diffraction pattern, physico-chemical and/or pharmacokinetic properties, and thermodynamic stability.

An embodiment of the present invention is directed to salts of N-[6-(cis-2,6-dimethylmorpholin-4-yl)pyridine-3-yl]-2-methyl-4'-(trifluoromethoxy)[1,1'-biphenyl]-3-carboxamide. In preferred embodiments, the salt is selected from the mono hydrochloride, diphosphate and mono sulfate salts of N-[6-(cis-2,6-dimethylmorpholin-4-yl)pyridine-3-yl]-2-methyl-4'-(trifluoromethoxy)[1,1'-biphenyl]-3-carboxamide. A particularly preferred embodiment of the of the present invention are the diphosphate and the mono sulfate salts of N-[6-(cis-2,6-dimethylmorpholin-4-yl)pyridine-3-yl]-2-methyl-4'-(trifluoromethoxy)[1,1'-biphenyl]-3-carboxamide.

The present invention may be used for treating carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine and endocrine pancreatic carcinoma), esophagus, stomach, gall bladder, cervix, thyroid, and skin (including squamous cell carcinoma); tumors of the central and peripheral nervous system including astrocytoma, neuroblastoma, glioma, medulloblastoma and schwannomas; tumors of mesenchymal origin including fibrosarcoma, rhabdomyosarcoma, and osteosarcoma; and other tumors including melanoma, Merkel cell carcinoma, xeroderma pigmentosum, keratoacanthoma, seminoma, thyroid follicular cancer, and teratocarcinoma. The present invention may also be used for treating mastocytosis, germ cell tumors, pediatric sarcomas, and other cancers.

The present invention is also useful for inhibiting the growth and proliferation of hematopoietic tumors of lymphoid lineage such as leukemia, including acute lymphocytic leukemia (ALL), acute lymphoblastic leukemia, B-cell lymphoma, T-cell lymphoma, Hodgkins lymphoma, non-Hodgkins lymphoma, hairy cell lymphoma, histiocytic lymphoma, and Burkitts lymphoma; and hematopoietic tumors of myeloid lineage including acute and chronic myelogenous leukemias (CML), myelodysplastic syndrome, myeloid leukemia, and promyelocytic leukemia.

EXAMPLE 1

Preparation of the Diphosphate Salt

To a 250 mL, three-necked reaction flask 7.0 g (0.0144 mole) of 2-methyl-4'-trifluoromethoxy-biphenyl-3-carboxylic acid [6-(cis-2,6-dimethyl-morpholin-4-yl)-pyridin-3-yl]-amide free base and acetonitrile (178.5 mL, HPLC grade) was added under nitrogen. The suspension was heated to 58° C. under nitrogen over 20 minutes to obtain a clear solution. To the reaction solution 3.403 g of 85% phosphoric acid in water (2 equiv) was added over 18 minutes. Within 5 minutes of the phosphoric acid addition, N-[6-(cis-2,6-dimethylmorpholin-4-yl)pyridine-3-yl]-2-methyl-4'-(trifluoromethoxy)[1,1'-biphenyl]-3-carboxamide di-phosphate precipitates out. The white slurry was stirred and cooled to room temp over 100 minutes. The slurry was then cooled to 0±5° C. over 5 minutes and stirred for 1 hour. The mixture was filtered under suction and solid was washed with acetonitrile (3×9.4 mL). The drug substance was dried under vacuum at 50° C. for 16 hours to obtain 9.63 g of the phosphate salt (yield: 98%).

EXAMPLE 2

Preparation for the Monosulfate Salt

To a 100 mL, three-necked reaction flask was charged 3.0 g (6.18 mmole) of N-[6-(cis-2,6-dimethylmorpholin-4-yl)pyridine-3-yl]-2-methyl-4'(trifluoromethoxy)[1,1'-biphenyl]-3-carboxamide free base and acetonitrile (35 mL, HPLC grade) under nitrogen. The suspension was heated to 50° C. under nitrogen over 30 minutes to obtain a clear solution. To the mixture was added a 1.5 mL of 6 M sulfuric acid (1.5 equiv) over 10 minutes. The mixture was stirred at 50° C. for 3 hours and allowed to cool to 25° C. over 25 minutes. Within 5 minutes the solids came out. The slurry was stirred at 25° C. for 16 hours. The mixture was filtered under suction and solid was washed with acetonitrile (10 mL). The drug substance was dried under vacuum at 55° C. for 16 hours to obtain 3.0 g of the sulfate salt (yield: 83%).

EXAMPLE 3

Preparation for the Monohydrochloride Salt

To a 100 mL, three-necked reaction flask was charged 3.0 g (6.18 mmole) of N-[6-(cis-2,6-dimethylmorpholin-4-yl)pyridine-3-yl]-2-methyl-4'-(trifluoromethoxy)[1,1'-biphenyl]-3-carboxamide free base and acetone (25 mL, HPLC grade) under nitrogen. The suspension was stirred at 25° C. under nitrogen for 30 minutes to obtain a clear solution. To the mixture was added a 1.5 mL of 6 M hydrochloric acid (1.5 equiv) over 10 minutes. Within 5 minutes the solids came out. The slurry was stirred at 25° C. for 16 hours. The mixture was filtered under suction and solid was washed with acetone (10 mL). The drug substance was dried under vacuum at 55° C. for 16 hours to obtain 3.0 g of the hydrogen chloride salt (yield: 93%).

EXAMPLE 4

Table 1 below shows stability measured by degradation products (or assay) and appearance color. DPs are analyzed by HPLC (method see Table 3). They are calculated as area-% products. Compositions of the mixtures in mass % are as follows. Mixture 1: Lactose 200 mesh/maize starch modified 1500 LM/Aerosil 200/Magnesiumstearate 78.5:20:0.5:1 (m/m/m/m). Mixture 2: Mannitol/Avicel PH 102/Cutina HR (57:38:5) (m/m/m).

TABLE 1

| | Salt Form | | | | | |
|---|---|---|---|---|---|---|
| | Phosphate, di | | Sulfate, mono | | Hydrochloride, mono | |
| Test Conditions | DP [%] | CL | DP [%] | CL | DP [%] | CL |
| Unstressed drug substance | | | | | | |
| Bulk | 1.02 | — | 0.42 | — | 0.30 | — |
| 0.2% solutions or suspensions, 2 week 50° C. | | | | | | |
| pH 1 | 0.99 | A ↓ | — | — | — | — |
| pH 3 | 1.07 | A ↓ | — | — | — | — |
| pH 5 | 1.04 | A ↓ | — | — | — | — |
| pH 7 | 1.06 | A ↓ | — | — | — | — |
| pH 9 | 1.05 | A ↓ | — | — | — | — |
| pH 11 | 1.03 | A ↓ | — | — | — | — |
| Water | 1.07 | A ↓ | 0.41 | A ↓ | 0.31 | A ↓ |
| Methanol | 1.02 | A * | 0.68 | A * | 2.06 | A * |
| Acetonitrile | 1.93 | A * | 0.44 | A * | 0.38 | A * |
| Acetonitrile/Water (50:50) | 1.10 | A * | 0.80 | A * | 1.72 | A * |
| 2% (or 5%) solutions or suspensions, 1 day room temperature | | | | | | |
| 0.5% CMC | — | | 0.45 | A ↓ | 0.33 | A ↓ |
| HPMC Cellulose 4000 0.5% | 1.04 | A ↓ | 0.47 | A ↓ | 0.32 | A ↓ |
| Tween 80, 0.8% | 1.07 | A ↓ | 0.43 | A ↓ | 0.31 | A ↓ |
| Solid state, 2 week 50° C., tight container | | | | | | |
| Bulk (HPLC) | 1.03 | A | 0.40 | A | 0.31 | A |
| Bulk (XRPD) | No change | — | No change | — | No change | — |
| Solid state, 2 week 80° C., tight container | | | | | | |
| Bulk (HPLC) | 1.06 | A | 0.43 | A | 0.35 | A |

TABLE 1-continued

| | Salt Form | | | | | |
|---|---|---|---|---|---|---|
| | Phosphate, di | | Sulfate, mono | | Hydrochloride, mono | |
| Test Conditions | DP [%] | CL | DP [%] | CL | DP [%] | CL |
| Bulk (DSC) | No change | — | No change | — | No change | — |
| *2 weeks 50° C., tight container* | | | | | | |
| 1% in mixture 1 | 0.96 | A | 0.41 | A | 0.27 | A |
| 1% in mixture 2 | 1.11 | A | 0.44 | A | 0.39 | A |
| *Solid state, 2 week 50° C./75% r.h.* | | | | | | |
| Bulk (HPLC) | 0.96 | A | 0.42 | A | 0.29 | A |
| Bulk (XRPD) | Slightly changed * | — | No change | — | No change | — |
| *Solid state, 2 week 80° C./75% r.h.* | | | | | | |
| Bulk (HPLC) | 1.02 | A | 1.34 | A | 0.35 | A |
| Bulk (XRPD) | Changed ** | — | No change | — | No change | — |
| *2 weeks 50° C./75% r.h.* | | | | | | |
| 1% in mixture 1 | 1.59 | A | 0.70 | A | 2.85 | A |
| 1% in mixture 2 | 1.01 | A | 0.41 | A | 0.31 | A |
| *Xenon light (approx. 1200 kLuxh)* | | | | | | |
| Bulk (HPLC) | 1.35 | A | 1.1 | A | 1.46 | B |
| Bulk (XRPD) | No change | — | No change | — | No change | — |
| *Bulk corrosivity* | | | | | | |
| 2 day 80% r.h. with stainless steel coupon | No visible change in the surface of the stainless steel coupon | | No visible change in the surface of the stainless steel coupon | | No visible change in the surface of the stainless steel coupon | |

* There is a new peak in the XRPD pattern when compared with the unstressed diphosphate.

** The XRPD pattern is similar to that of phosphate, yet with one extra peak.

↓ Suspension

* Clear solution after stress test

— Test not performed

A No change of color

B Slight discoloration

C Medium discoloration

D Strong discoloration

EXAMPLE 5

Table 2 below shows chemical and physico-chemical characteristics.

TABLE 2

| | Salt Form | | | | | |
|---|---|---|---|---|---|---|
| | Phosphate, di | | Sulfate, mono | | Hydrochloride, mono | |
| Parameter | calcul. | found | calcul. | found | calcul. | found |
| Elementary analysis | | | | | | |
| % C | 45.82 | 46.06 | 53.51 | 53.28 | 59.83 | 60.11 |
| % H | 4.73 | 5 | 4.84 | 4.91 | 5.21 | 5.06 |
| % F | 8.36 | 8.35 | 9.77 | 9.44 | 10.92 | 10.69 |

TABLE 2-continued

| | Salt Form | | | | | |
|---|---|---|---|---|---|---|
| | Phosphate, di | | Sulfate, mono | | Hydrochloride, mono | |
| Parameter | | | | | | |
| Elementary analysis | calcul. | found | calcul. | found | calcul. | found |
| % N | 6.17 | 6.08 | 7.2 | 7.08 | 8.05 | 7.88 |
| % O | 25.82 | 25.29 | 19.19 | 20.29 | 9.2 | 9.93 |
| % P | 9.09 | 9.22 | | | | |
| % S | | | 5.49 | 5.68 | . | . |
| % Cl | | | | | 6.79 | 6.33 |
| DSC-Purity | | | | | | |
| Heating rate 10° C./min | N/A | | N/A | | N/A | |
| HPLC-Purity (e.g. area-%) | | | | | | |
| | 1.02 | | 0.42 | | 0.30 | |
| Melting point (DSC) | | | | | | |
| Heating rate [° C./min] | 10 | | 10 | | 10 | |
| Melting enthalpy (J/g) | N/A | | N/A | | N/A | |
| pH of 1% solution or suspension | | | | | | |
| In water | 2.02 | | 1.45 | | 1.69 | |
| Solubility (approx. at 25° C., mg/ml) | | | | | | |
| 0.1N HCL | 0.004 (Final pH 1.04) | | 0.003 (Final pH 1.09) | | 0.002 (Final pH 1.02) | |
| Phosphate buffer, pH 6.8 | 0.001 (Final pH 2.86) | | 0.002 (Final pH 1.82) | | 0.000 (Final pH 5.93) | |
| Water | 0.009 (Final pH 1.94) | | 0.007 (Final pH 1.26) | | 0.005 (Final pH 1.67) | |
| Methanol | >40 | | 24.4 | | >40 | |
| Ethanol | 19.7 | | 19.7 | | 56.4 | |
| 2-Propanol | 14.3 | | 4 | | 10.3 | |
| Acetone | 2.8 | | 1.7 | | 3.2 | |
| Ethyl Acetate | 0.3 | | 0.09 | | 2.5 | |
| Acetonitrile | 0.4 | | 1.4 | | 4.1 | |
| Thermogravimetry (weight loss in %) | | | | | | |
| Heating rate 10° C./min (%) | 0.19% at 150° C. | | 1.89% at 150° C. | | 0.48% at 150° C. | |
| Residual solvents (%) | | | | | | |
| | Heptane: 0.0001463, Acetonitrile, | | Acetonitrile: 0.419087, Water: 1.36, | | Acetone: 0.0002356, Water: 0.4,. | |
| Intrinsic dissolution rate (mg min$^{-1}$ cm$^{-2}$) | | | | | | |
| HCl 0.1N | — | | — | | — | |
| Water | — | | — | | — | |
| Water + Surfactant (SDS) | — | | — | | — | |
| NMR | Chemical shift changed | | Chemical shift changed | | Chemical shift changed | |

* Attempts to measure intrinsic dissolution rate were not successful due to low solubility.

EXAMPLE 6

Table 3 below shows morphic properties.

TABLE 3

| | Salt form | | |
|---|---|---|---|
| Parameter | Phosphate, di | Sulfate, mono | Hydrochloride, mono |
| Thermal properties | | | |
| *As is* | | | |
| DSC | 213° C. | N/A | N/A |
| XRPD (crystallinity) | Crystalline | Crystalline | Crystalline |
| *After heating and cooling-* | | | |
| DSC | N/A | N/A | N/A |
| XRPD | N/A | N/A | N/A |
| Hygroscopicity | | | |
| *As is* | | | |
| Loss on drying by TGA (%) | 0.19 at 150° C. | 1.89 at 150° C. | 0.48 at 150° C. |
| *DVS* | | | |

| RH (%) | Sorp. Weight % chg. | Desorp. Weight % chg. | Sorp. Weight % chg. | Desorp. Weight % chg. | Sorp. Weight % chg. | Desorp. Weight % chg. |
|---|---|---|---|---|---|---|
| 0.0 | 0.000 | −0.038 | 0.000 | 1.007 | −0.0001 | −0.0114 |
| 25.0 | 0.059 | 0.136 | 1.232 | 1.256 | 0.3334 | 0.3799 |
| 50.0 | 0.149 | 0.341 | 1.455 | 1.495 | 0.4660 | 0.4932 |
| 75.0 | 0.270 | 1.268 | 1.634 | 1.716 | 0.5753 | 0.6069 |
| 85.0 | 0.400 | 1.828 | 1.835 | | 0.6525 | 0.6817 |
| 95.0 | 3.420 | 3.420 | 2.330 | 2.330 | 0.8784 | 0.8784 |

| | Phosphate, di | Sulfate, mono | Hydrochloride, mono |
|---|---|---|---|
| XRPD after DVS test | No change | No change | No change |
| Crystal modification after 72 hours vibration | | | |
| | DSC/XRPD/TG | DSC/XRPD/TG | DSC/XRPD/TG |
| Water | XRPD pattern changed, different than free base. Final pH 1.94 | Dissociated to free base. Final pH 1.26 | Dissociated to free base Final pH 1.94 |
| pH 6.8 buffer | XRPD pattern changed, different than free base. Final pH 2.86 | Dissociated to free base Final pH 1.82 | No form change Final pH 5.93 |
| pH 3 buffer | XRPD pattern changed, different than free base. Final pH 2.15 | Dissociated to free base Final pH 2.00 | Dissociated to free base Final pH 2.89 |
| 0.1N HCl solution | XRPD pattern changed, different than free base. | XRPD pattern changed, different than that of free base. | XRPD pattern changed, different than that of free base. |
| Methanol | — | Y, crystalline to crystalline | — |
| Ethanol | XRPD pattern changed, poorer crystalline than the original. | N, no form change | N, no form change |
| Iso Propanol | N, no form change | N, no form change | N, no form change |
| Ethyl acetate | N, no form change | N, no form change | N, no form change |
| Acetone | N, no form change | Y, crystalline to crystalline | N, no form change |
| Acetonitrile | N, no form change | N, no form change | N, no form change |
| Effect of grinding | | | |
| | No change in XRPD | No change in XRPD | No change in XRPD |
| Effect of compression | | | |
| | No change in XRPD | No change in XRPD | No change in XRPD |

N—no, Y—yes

EXAMPLE 7

Rat TK data of N-[6-(cis-2,6-dimethylmorpholin-4-yl)pyridine-3-yl]-2-methyl-4'-(trifluoromethoxy)[1,1'-biphenyl]-3-carboxamide diphosphate dosed as a suspension, with a 10-fold increase in dose, showed a 3.1-fold increase in exposure from 10 to 100 mpk. The inter-subject exposure is slightly variable, especially at high dose (100 mpk). See Table 4.

TABLE 4

| Dose (mg/kg) | Rat | $AUC_{0-24}$ (ng*h/mL) | $AUC_{0-24}$/dose (ng*h/mL)/ (mg/kg/day) | $C_{max}$ (ng/mL) | $C_{max}$/dose (ng/mL)/ (mg/kg/day) | $t_{max}$ (h) |
|---|---|---|---|---|---|---|
| 10 | 001 | 43300 | 4330 | 2820 | 282 | 8.00 |
|  | 002 | 52800 | 5280 | 3160 | 316 | 8.00 |
|  | 003 | 49400 | 4940 | 3100 | 310 | 4.00 |
| 100 | 004 | 232000 | 2320 | 14800 | 148 | 8.00 |
|  | 005 | 96800 | 968 | 4520 | 45.2 | 8.00 |
|  | 006 | 131000 | 1310 | 7490 | 74.9 | 8.00 |

EXAMPLE 8

A suspension formulation of the free form and the diphosphate salt of N-[6-(cis-2,6-dimethylmorpholin-4-yl)pyridine-3-yl]-2-methyl-4'-(trifluoromethoxy)[1,1'-biphenyl]-3-carboxamide are dosed to rat at 3 mpk and 2.1 mpk, respectively. It was found that the disphosphate salt provided a large increase in exposure (16-fold increase) compared to the free form as outline in Table 5.

TABLE 5

| | 2.1 mg/kg PO dose in suspension Diphosphate salt | | 3.0 mg/kg PO dose in suspension Free base * | | IV 3 mg/kg** Free base | |
|---|---|---|---|---|---|---|
| PK Parameter | Mean | SD | Mean | SD | Mean | SD |
| AUClast (nM*h) | 5747 | 1395 | 510 | 153 | 17500 | n = 2 |
| AUClast/dose (nM*h)/mg/kg | 2737 | 664 | 170 | 51 | 5830 | n = 2 |
| $AUC_{inf}$(nM*h) | 5917 | 1451 | 512 | 140 | 17500 | n = 2 |
| $AUC_{inf}$/dose(nM*h)/mg/kg | 2818 | 691 | 171 | 46.7 | 5840 | n = 2 |
| $C0/C_{max}$(nM) | 947 | 167 | 237 | 76.3 | 6108 | n = 2 |
| $C_{max}$/dose (nM/mg/kg) | 451 | 79.3 | 78.9 | 25.4 | | |
| $T_{max}$ (h) | 2.00 | 0.00 | 0.500 | 0.00 | | |
| % F | 48% | | 3% | | | |

EXAMPLE 9

Details about Methodology, Instruments and Standards Used in Examples 4-5

1 pH Value

The pH was determined by transferring approximately 10 mg of N-[6-(cis-2,6-dimethylmorpholin-4-yl)pyridine-3-yl]-2-methyl-4'-(trifluoromethoxy) [1,1'-biphenyl]-3-carboxamide salt to a 20 mL vial and adding 10 mL of the corresponding buffer or water. The solutions were stirred continuously as the pH was measured.

2 Determination of Approximate Solubility

Excess salts were equilibrated in solvents for 1 day at 25±0.5° C. Slurries were filtered and the filtrate saved for HPLC solubility determination.

3 Hygroscopicity

Sorption/desorption isotherms: Instrument, Surface Measurement System DVS-1 temperature at 25±0.5° C.

4 Polymorphism Behavior

Slurries of N-[6-(cis-2,6-dimethylmorpholin-4-yl)pyridine-3-yl]-2-methyl-4'-(trifluoromethoxy)[1,1'-biphenyl]-3-carboxamide salts were stirred at high speed for 24 hours at 25±0.5° C. The slurries were filtered and the solids collected for XRPD analyses.

5 HPLC Method

Column: Symmetry C18, 3.5 micrometer particle diameter, 4.6×75 mm (Waters)
Column temperature: 35 degrees
Flow rate: 1 mL/min
Mobile phase: A=0.1% TFA in water, and B=acetonitrile
Gradient table shown below in Table 6:

TABLE 6

| Time (min) | Flow (mL/min) | % A | % B |
|---|---|---|---|
| 1 |  | 1.00 | 85 | 15 |
| 2 | 10 | 1.00 | 15 | 85 |
| 3 | 10.5 | 1.00 | 15 | 85 |
| 4 | 10.6 | 1.00 | 85 | 15 |

Stability Sample Preparation for HPLC Analysis:

For phosphate in pH 1 buffer solution, acetonitrile was added to dilute the 0.2% slurry to 0.1% clear solution. For phosphate in the rest of buffer solutions, tetrahydrofuran was added to dilute the 0.2% slurry to 0.1% clear solution. For salts in water, acetonitrile was added to dilute the 0.2% slurry to 0.1% clear solution. For salts in methanol, acetonitrile or acetonitrile/water (50:50, v/v), the corresponding solvent or solvent mixture was added to dilute the 0.2% slurry to 0.1% clear solution. For salts in 0.5% CMC, HPMC cellulose 4000 0.5%, or Tween 80, 0.8%, tetrahydrofuran and water were added to dilute the 2% slurry to 0.1% clear solution and to reach tetrahydrofuran/water 50:50 (v/v). For bulk stability samples (including the samples in excipient mixtures), acetonitrile/water (80:20, v/v) was added to make 0.1% clear solution.

EXAMPLE 10

The sulfate salt and diphosphate salt of N-[6-(cis-2,6-dimethylmorpholin-4-yl)pyridine-3-yl]-2-methyl-4'-(trifluoromethoxy)[1,1'-biphenyl]-3-carboxamide (Compound A in Table 7 below) are dosed as a suspension at 1 mg/mL in 0.5% Methyl Cellulose/0.5% Tween 80 at a dosing volume of 10 mL/kg to Wistar rats. The diphosphate salt was found to give 1.6× more exposure in terms of AUC (0-24 hours) ng*hr/mL when compared to the sulfate salt. Results are shown below in Table 7.

TABLE 7

| Compound | Dose (mg/kg) | Rat | $AUC_{0-24}$ (ng*h/mL) | $AUC_{0-24}$/dose (ng*h/mL)/ (mg/kg/day) | $C_{max}$ (ng/mL) | $C_{max}$/Dose (ng/mL)/ (mg/kg/day) | $t_{max}$ (h) |
|---|---|---|---|---|---|---|---|
| Compound A Sulfate | 10 | 1b | 25900 | 2590 | 1900 | 190 | 4 |
|  |  | 2b | 28700 | 2870 | 1860 | 190 | 2 |
|  |  | 3b | 36200 | 3620 | 3560 | 360 | 1 |
| Compound A Diphosphate | 10 | 001 | 43300 | 4330 | 2820 | 282 | 8 |
|  |  | 002 | 52800 | 5280 | 3160 | 316 | 8 |
|  |  | 003 | 49400 | 4940 | 3100 | 310 | 4 |

As shown in Table 7, the mean tmax for sulfate salt is shorter (2.3 hours) versus diphosphate salt (6.7 hours). The mean cmax/dose for phosphate is 303 and for sulfate is 244. The mean auc/dose for phosphate is 4850, for sulfate is 3030. Overall, the sulfate salt showed less exposure in-vivo (about 40% less) than the diphosphate salt.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A diphosphate salt of N-[6-(cis-2,6-dimethylmorpholin-4-yl)pyridine-3-yl]-2-methyl-4'-(trifluoromethoxy)[1,1'-biphenyl]-3-carboxamide.

2. A pharmaceutical composition comprising:
   (a) a therapeutically effective amount of a salt according to claim 1; and
   (b) at least one pharmaceutically acceptable carrier, diluent, vehicle or excipient.

* * * * *